United States Patent [19]

Hackenbruch et al.

[11] Patent Number: 4,968,845

[45] Date of Patent: Nov. 6, 1990

[54] PROCESS FOR THE PREPARATION OF HALOGEN-CONTAINING AROMATIC COMPOUNDS

[75] Inventors: Joachim Hackenbruch, Ginsheim-Gustavsburg; Theodor Papenfuhs, Frankfurt am Main; Klaus Warning, Eppstein/Taunus; Gunter Siegemund, Hofheim am Taunus, all of Fed. Rep. of Germany

[73] Assignee: Hoechst Aktiengesellschaft, Frankfurt am Main, Fed. Rep. of Germany

[21] Appl. No.: 320,062

[22] Filed: Mar. 7, 1989

[30] Foreign Application Priority Data

Mar. 9, 1988 [DE] Fed. Rep. of Germany ....... 3807623

[51] Int. Cl.$^5$ .............................................. C07C 45/46
[52] U.S. Cl. ...................... 568/323; 568/332
[58] Field of Search ................. 568/319, 323, 322

[56] References Cited

U.S. PATENT DOCUMENTS

| | | | |
|---|---|---|---|
| 3,907,837 | 9/1975 | Effenberger et al. | 568/323 |
| 4,487,934 | 12/1984 | Shutske et al. | 568/323 |
| 4,827,041 | 5/1989 | Ford et al. | 568/322 |

FOREIGN PATENT DOCUMENTS

| | | | |
|---|---|---|---|
| 0075390 | 3/1983 | European Pat. Off. | 568/319 |
| 2139994 | 2/1973 | Fed. Rep. of Germany | 568/309 |
| 3531837 | 3/1987 | Fed. Rep. of Germany | 568/319 |
| 1139296 | 1/1969 | United Kingdom | 568/319 |
| 1378913 | 12/1974 | United Kingdom | 568/309 |

OTHER PUBLICATIONS

P. M. Hergenrother et al., J. Polymer Sci.; Polymer Chemistry, 25:1093, 1094 (1987).

Primary Examiner—James H. Reamer

[57] ABSTRACT

A process for the preparation of halogen-containing aromatic compounds of the formula

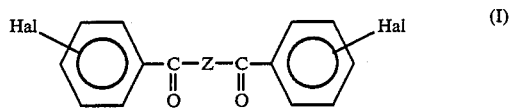

wherein Hal represents fluorine, chlorine or bromine and Z represents an aromatic group which comprises reacting a halobenzene of the formula $C_6H_5Hal$ (II) under anhydrous conditions with a halide of a bisacid having the formula Hal-CO-Z-CO-Hal (III) in a molar ratio of at least 2:1 in the presence of a haloalkane sulfonic acid of the formula $Y(C_nX_{2n})SO_3H$ (IV), in formulae II and III Hal and Z having the afore-mentioned meaning and Y representing fluorine or hydrogen, X at least one of fluorine and chlorine, but at least one X being fluorine, and n being an integer of from 1 to 10.

The said bis-(4-halobenzoyl) compounds being useful monomers for chemically resistant plastics which are still resistant even at high temperatures.

21 Claims, No Drawings

PROCESS FOR THE PREPARATION OF HALOGEN-CONTAINING AROMATIC COMPOUNDS

DESCRIPTION

The invention relates to a process for the preparation of halogen-containing aromatic compounds which contain at least two aromatic rings which are bonded to one another via at least one bridging member.

The preparation of 1,4-bis-(4-chlorobenzoyl)-benzene is disclosed in GB Patent 1,139,296, where 700 parts (6.22 mol) of chlorobenzene are reacted at 130° C in the course of 6 hours with 97 parts (0.48 mol) of terephthaloyldichloride and 145 parts (1.09 mol) of powdered anhydrous aluminum chloride. A yield is not reported. The analogous reaction of fluorobenzene is described, inter alia, in DE-A-3,531,837, the halobenzene (in this case fluorobenzene), aluminum chloride and terephthaloyl dichloride being used in virtually the same molar ratios as in GB Patent 1,139,296. However, the yield reported for 1,4- bis-(4-fluorobenzoyl)-benzene in DE-A-3,531,837 is dubious since more product is obtained after purification (1250 g) than was present as crude product (1225 g). Also, the melting point is incorrectly reported as 121°C. (instead of 218.5 to 219.5°C. according to Hergenrother et al. in Journ. Pol. Sci., part A, Polymer Chemistry, 25. 1094 (1987)).

It is a disadvantage of all previously known processes that a large amount of aluminum trichloride must be employed which must be led off with the effluent during working-up and pollutes the same. This also applies to the other Lewis acids iron chloride, titanium tetrachloride and tin tetrachloride mentioned in DE-A3,531,837. It is therefore desirable to develop a process where the catalyst systems are used in sub-stoichiometric amounts and are easily worked up and can be recovered. Effenberger et al. in DE-A-2,139,994 describe a step in this direction with the preparation of aromatic ketones in the presence of less than the molar amount of perfluoroalkanesulfonic acids, monoketones being prepared in good yields in all 8 examples. It is disadvantageous here, however, that the reaction mixture already has to be treated with water to recover the catalyst after use once. The present invention accordingly relates to a process for the preparation of halogen-containing aromatic compounds of the formula I which is set forth below, in which Hal denotes fluorine, chlorine or bromine and Z denotes an aromatic grouping, which comprises reacting a halobenzene of the formula $C_6H_5Hal$ (II) under anhydrous conditions with a bis(acid halide) of the formula Hal—CO—Z—CO—Hal (III) in a molar ratio of at least 2:1 in the presence of haloalkanesulfonic acids of the formula $Y(C_nX_{2n})SO_3H$ (IV), preferably of the formula $Y(C_nF_{2n})SO_3H$ (V), where Hal and Z in the formulae II and III have the meaning previously indicated and Y denotes fluorine or hydrogen, X denotes fluorine and/or chlorine and n denotes an integer from 1 to 10, at least one X standing for fluorine.

The invention also relates to a clear solution of the compound of formula I

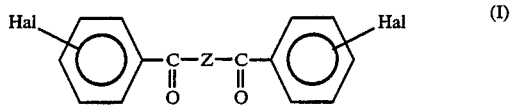

wherein Hal represents fluorine, chlorine or bromine and Z represents an aromatic group, in diphenylsulfone for the preparation of polycondensates, said solution having been clarified by a treatment with a solid base. A solution in which the treatment has been effected with $Na_2CO_3$, $K_2CO_3$ or MgO is preferred, particularly where the compound of the formula I is 1,4-bis-fluorobenzoylbenzene or 1,4-bis-chlorobenzoylbenzene.

The preparation of compounds I which has at least one of the features that Hal is fluorine or chlorine and Z is phenylene, expediently other than in the ortho-position, in particular p-phenylene and that halogen is in a position other than the o-position to the CO group is preferred. Compounds having halogen in the p-position are very particularly preferred.

A suitable halobenzene of the formula II is, for example, bromobenzene. However, fluorobenzene and chlorobenzene are preferred. The halobenzene is preferably used in excess, so that it serves as a solvent for the bis(acid halide) III. In general, 6 to 40, preferably 10 to 30, moles of halobenzene II are employed per mole of bis(acid halide) III. In the bis(acid halide) III, Z is, in addition to the phenylene radical, for example, the radical $C_5H_4$-E-$C_5H_4$ with E=O, $(CG_2)_m$, CO, S, SO, $SO_2$ or $Si(CH_3)_2$, where G is hydrogen, methyl, fluorine or trifluoromethyl and m is an integer from 0 to 4. If m is 0, the two phenylene radicals are thus bonded to one another by a single bond. Examples of bis(acid halides) which may be mentioned are: terephthaloyl dichloride, isophthaloyl dichloride, 1,4-and 2,6-naphthalenedicarbonyl dichloride, 1,5-anthracenedicarbonyl dichloride, 4,4,-biphenyldicarbonyl dichloride, bis-(4,4,-chlorocarbonylphenyl)-methane, 2,2--bis-(4,4'-chlorocarbonylphenyl)-propane, hexafluoro-2,2- bis-(4,4'-chlorocarbonylphenyl) propane, di-(4,4,-chlorocarbonylphenyl) ketone, di-(4,4,-chlorocarbonylphenyl) ether, di-(4,4,-chlorocarbonylphenyl) sulfide, di-(4,4',chlorocarbonylphenyl) sulfoxide and di-(4,4',-chlorocarbonylphenyl) ketone, 4,4,-biphenyldicarbonyl dichloride, di-(4,4,-chlorocarbonylphenyl) ether, di-(4,4'-chlorocarbonylphenyl) sulfide and di-(4,4,-chlorocarbonylphenyl) sulfone are preferred.

The compounds of the formula II and the formula III mentioned as examples are either known or can be prepared by analogous processes.

The end products obtained of the formula I are for example 1,4-bis-(4-fluorobenzoyl)-benzene, 1,4-bis-(4-chlorobenzoyl)-benzene, 4,4,-bis-(4-fluorobenzoyl)-diphenyl ether, 4,4,-bis-(4-fluorobenzoyl)-biphenyl, 4,4,-bis-(4-fluorobenzoyl)-diphenyl sulfide and 4,4,-bis(4-fluorobenzoyl)-diphenyl sulfone.

The process according to the invention is in general carried out at temperatures from 20 to 200° C, preferably from 60 to 180° C and advantageously also under oxygen-free conditions. The process can be carried out at atmospheric pressure, but also at a slight excess pressure, in particular up to the intrinsic pressure of the system, which is determined, in particular, by the temperature used, but also by other factors, such as the extent of filling of the reaction vessel. For example, it may be in the range up to 10 or 15 bar. If the process is carried out at elevated pressure, the process can, for example, be carried out in a stainless steel autoclave which is optionally lined with a resistant material such as polytetrafluoroethylene. The reaction can be accelerated by the use of excess pressure, but this may be accompanied by increased formation of by-products.

It is also possible to additionally use solvents which are inert to the reaction participants under the reaction conditions, for example aliphatic hydrocarbons or halogen derivatives thereof. Usually, however, these are not accompanied by any advantages.

An advantage of the process according to the invention is that the bis(acid halides) III and fresh halobenzene are again added to the mother liquor obtained after the separation of the precipitated bis-(4-halobenzoyl) compound and can thus be reused many times as a reaction medium, for example up to 10 times, without noticeable losses of yield occurring. On too frequent recycling, for example after the tenth recycling, an increase in by-products, in particular partial reaction products, is observed, so that the reaction mixture must then be worked up, it being possible for the catalyst to be recovered by customary methods, for example according to DE-A-2,139,994 (=GB Patent 1,378,913). The possibility of utilizing the mother liquor repeatedly can naturally also be accomplished in such a way that a small part, for example 5 to 20%, is excluded after each addition and replaced by new solvent and catalyst.

The catalysts of the formula (IV) used according to the invention preferably contain not more than 3 chlorine atoms, in particular at most one chlorine atom. The group $C_nX_{2n}$ or $C_nF_{2n}$ may be straight-chain or branched, compounds in which Y is hydrogen frequently containing the latter in the $\beta$-position. The perfluorinated catalysts used according to the invention are known (cf. DE-A-2,139,994), like the $\beta$-H-perfluoroalkanesulfonic acids (J. Am. Chem. Soc. 75, 4595–4596 (1953). If they are not yet known, they can be obtained by customary processes. If they are employed in the process according to the invention in amounts which are too low, namely in the region of amounts from 0.01 to 10 moles % used in DE-A-2,139,994 in the examples, the desired bis-(4-halobenzoyl) compounds are not obtained or are only obtained in low yields, or too greatly contaminated, as is illustrated by the comparison experiments C1 and C2. Suitable compounds of the formula IV . are, for example, perfluoro-n-octanesulfonic acid, perfluorohexanesulfonic acid, perfluorobutanesulfonic acid, pentafluoroethanesulfonic acid, $\beta$-H-perfluoroheptanesulfonic acid and $\beta$-H-perfluoropentanesulfonic acid. Naturally, mixtures of different catalysts may also be used. Trifluoromethanesulfonic acid, 2-chloro-1,1,2-trifluoroethanesulfonic acid, 2-hydroperfluoroethanesulfonic acid and/or 2-hydroperfluoropropanesulfonic acid are preferred. In general, the catalyst, is added to the first batch in amounts from 15 to 500 mole %, preferably from 50 to 150mole %, relative to the bis(acid halide) III. If the mother liquor is used again, after separating off the desired reaction product, by recycling it, no additional catalyst needs to be added so that, as a rule, a far lower amount of catalyst is used as a result than corresponds, for example, to half the stoichiometric amount.

The bis-(4-halobenzoyl) compounds obtained by the process according to the invention, of which 1,4-bis-(4-fluorobenzoyl)-benzene and 1,4-bis-(4-chlorobenzoyl)-benzene are preferred, are useful monomers for chemically resistant plastics which are still resistant even at high temperatures. They may be used directly, without further purification, for polycondensations after dissolving in suitable solvents, if appropriate with the addition of solid bases, preferably $Na_2CO_3$, $K_2CO_3$ or MgO, and subsequent filtration if necessary, for example with hydroquinone to give polyether ketones.

The invention is illustrated by the examples below. In these, h denotes hours and BFB denotes 1,4-bis-(4-fluorobenzoyl) benzene.

EXAMPLES (1) 1730 g (18 mol) of fluorobenzene, 203 g (1 mol) of terephthaloyl dichloride and 150 g (1 mol) of trifluoromethanesulfonic acid were initially introduced at room temperature and the mixture was heated under reflux (b.p. 85° C) for 20 h. The reaction mixture was stirred until cool, and the precipitated 1,4-bis-(4-fluorobenzoyl)benzene (BFB) was filtered off and washed with 192 g (2 mol) of fluorobenzene. The mother liquor containing the catalyst and the washing solution were combined, 203 g of terephthaloyl dichloride were added and the reaction was repeated in the manner indicated. The mother liquor could be recycled ten times without a noticeable reduction in yield being ascertainable. In order to determine the purity, a small amount of the crude product which was moist as a result of adhering fluorobenzene was dried and investigated by means of high pressure liquid chromatography. The yield, relative to the dicarboxylic acid halide, was 95.1% of theory after recycling ten times; m.p. 218–221°C.

The product could be further processed as follows: 450 g of the moist BFB was slowly heated with 600 g of diphenyl sulfone (DPS) and 10 g of MgO. After distilling off the fluorobenzene, the reaction mixture was heated to 200°C. for an hour and subjected to a clarifying filtration. The BFB obtained as diphenyl sulfone solution could be subjected to a polycondensation directly without further purification. The yield, relative to BFB, was 90%, and the purity (without DPS) was above 99%.

500 ml of water was added to the 1820 g of mother liquor remaining after recycling ten times; precipitated solid was separated off from the mixture, the two liquid phases were separated, 61.5 g (1.1 mol) of KOH was added to the aqueous phase, the water was separated off on a rotary evaporator, 200 g of $H_2SO$. (98.4% strength) were added to the residue and the trifluoromethanesulfonic acid was distilled off at atmospheric pressure. 92 g (=61% of theory) of trifluoromethanesulfonic acid were recovered.

(2) 575 g (6 mol) of fluorobenzene, 101.5 g (0.5 mol) of terephthaloyl dichloride and 75 g (0.5 mol) of trifluoromethanesulfonic acid were reacted as in Example 1. The yield after recycling 6 times was 93% of theory, and the purity was above 96%; m.p.: 218–220°C.

(3) 575 g (6 mol) of fluorobenzene, 101.5 g (0.5 mol) of terephthaloyl dichloride and 37.5 g (0.25 mol) of trifluoromethanesulfonic acid were reacted as in Example 1. The yield after recycling 7 times was 85.5% of theory, and the purity was above 96%; m.p.: 218–220°C.

(4) 575 g (6 mol) of fluorobenzene, 101.5 g (0.5 mol) of terephthaloyl dichloride and 18.8 g (0.125 mol) of trifluoromethanesulfonic acid were reacted as in Example 1. The yield after recycling 6 times was 81.3% of theory, and the purity was above 95%; m.p.: 218–220°C.

(5) 575 g (6 mol) of fluorobenzene, 101.5 g (0.5 mol) of terephthaloyl dichloride and 116 g (0.5 mol) of 2-hydroperfluoropropanesulfonic acid were reacted as in Example 1. The yield after recycling 6 times was 94.6% of theory and the purity was above 96%; m.p. 218–220°C.

(6) 575 g (6 mol) of fluorobenzene, 101.5 g (0.5 mol) of terephthaloyl dichloride and 78 g (0.25 mol) of 2-hydroperfluoropropanesulfonic acid were reacted as in Example 1. The yield after recycling 5 times was 91.7% of theory and the purity was above 95%; m.p. 218–220°C.

On processing further as in Example 1, a BFB dissolved in diphenyl sulfone was obtained, which could be used for the polycondensation without further purification. The yield was 89.3% (relative to BFB) and the purity (without solvent) was above 98%.

(7) 575 g (6 mol) of fluorobenzene, 101.5 g (0.5 mol) of terephthaloyl dichloride and 99.3 g (0.5 mol) of 2-chloro-1,1,2-trifluoroethanesulfonic acid were reacted as in Example 1. The yield after recycling 4 times was 96.6% of theory and the purity was 95%; m.p. 218–220°C.

(8) 575 g (6 mol) of fluorobenzene, 101.5 g (0.5 mol) of terephthaloyl dichloride and 91 g (0.5 mol) of 2-hydroperfluoroethanesulfonic acid were reacted as in Example 1. The yield after recycling 2 was 95.7% of theory and the purity was 96%; m.p. 218–220°C.

(9) 288 g (3 mol) of fluorobenzene, 31.5 g (0.15 mol) of terephthaloyl dichloride and 40.1 g (0.1 mol) of perfluorohexanesulfonic acid were reacted as in Example 1. The yield was 45% of theory after recycling once and the purity was about 80%. The residue consisted principally of perfluorohexanesulfonic acid.

(10) g (2 mol) of fluorobenzene, 20.3 g (0.1 mol) of terephthaloyl dichloride and 5 g (0.033 mol) of trifluoromethanesulfonic acid were heated at 140°C. for 8 hours in a 400 ml autoclave having a polytetrafluoroethylene lining. After completion of the reaction, the mixture was stirred until it had cooled to room temperature, the resulting hydrochloric acid was released and the mixture was filtered. The reaction product was washed with 20 g of fluorobenzene; the combined mother liquor was then again reacted with 20.3 g of terephthaloyl dichloride. The mother liquor was then recycled in the known course of the process. The yield after recycling 3 times was 95% of theory and the purity was 95%; m.p. 217–219°C.

(11) 674 g (6 mol) of chlorobenzene, 101.5 g (0.5 mol) of terephthaloyl dichloride and 75 g (0.5 mol) of trifluoromethanesulfonic acid were heated under reflux for 20 h. After stirring until cool, the precipitated 1,4-bis-(4chlorobenzoyl)benzene was filtered off with suction and washed with 112 g (1 mol) of chlorobenzene. The mother liquor and the filtrate obtained on washing were combined, 101.5 g of terephthaloyl dichloride were added and the mixture was heated under reflux for a further 20 h. The mother liquor was recycled five times in the way described. The yield was 71% of theory and the purity without chlorobenzene was above 99%; m.p.: 255–257°C.

COMPARISON EXAMPLES (C1) 575 g (6 mol) of fluorobenzene and 101.5 g (0.5 mol) of terephthaloyl dichloride and 0.75 g (0.005 mol) of trifluoromethanesulfonic acid were heated under reflux for 20 h. The crude product was filtered off and washed. BFB was obtained in a yield of less that 10%; the purity was only about 50%.

(C2) g (6 mol) of fluorobenzene, 101.5 g (0.5 mol) of terephthaloyl dichloride and 7.5 g (0.05 mol) of trifluoromethanesulfonic acid were heated under reflux for 20 h. After stirring until cool, the precipitate was filtered off and the reaction product was washed with 50 g of fluorobenzene. 101.5 g (0.5 mol) of terephthaloyl dichloride were added to the mother liquor and washing solution and the mixture was reacted as in Example 1. The yield after recycling 3 times was above 40% and the purity was about 60%.

We claim:

1. A process for the preparation of halogen-containing aromatic compounds of the formula

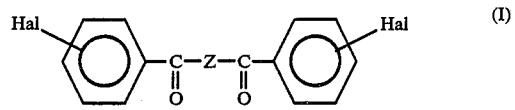

wherein Hal represents fluorine, chlorine or bromine and Z represents an aromatic group which comprises reacting a halobenzene of the formula C6H5Hal (II) under anhydrous conditions with a halide of a bisacid having the formula Hal-CO-Z-CO-Hal (III) in a molar ratio of at least 2:1 in the presence of from 15 to 500 mole-%, referring to the halide of the bisacid III, of a haloalkane sulfonic acid of the formula $Y(C_nX_{2n})SO_3H$ (IV), in formulae II and III Hal and Z having the aforementioned meaning and Y representing fluorine or hydrogen, X at least one of fluorine and chlorine, but at least one X being fluorine, and n being an integer of from 1 to 10.

2. A process as claimed in claim 1, wherein the mother liquor is separated from the compound I, and halide of a bisacid III and halobenzene II are then added thereto for a further batch of the reaction.

3. A process as claimed in claim 2, wherein a small part of the mother liquor is separated and replaced by a corresponding amount of the fresh components contained in the mother liquor.

4. A process as claimed in claim 1, wherein 6 to 40 moles of halogenzene II are applied per mole of compound III.

5. A process as claimed in claim 1, wherein 10 to 30 moles of halobenzene II are applied per mole of compound III.

6. A process as claimed in claim 1, wherein Z represents an aromatic group of the formula C6H4-E-C6H4 (VI), wherein E represents O, (CG2)m, CO, S, SO, SO2 or Si(CH3)2, G represents hydrogen, methyl, fluorine or trifluoromethyl and m represents 0 or an integer of from 1 to 4.

7. A process as claimed in claim 1, wherein in formulae I and II Hal represents fluorine or chlorine.

8. A process as claimed in claim 1, wherein in formulae I and III Z represents phenylene.

9. A process as claimed in claim 8, wherein Z represents phenylene other than o-phenylene.

10. A process as claimed in claim 9, wherein Z represents p-phenylene.

11. A process as claimed in claim 1, wherein in formulae I and III halogen is in a position other than the orthoposition to CO.

12. A process as claimed in claim 11, wherein the halogen is in the p-position to CO.

13. A process as claimed in claim 1, wherein as a haloalkane sulfonic acid a compound of the formula $Y(C_nF_{2n})SO_3H$ (V) is used, wherein Y represents fluorine or hydrogen.

14. A process as claimed in claim 1, wherein in a compound of the formula IV Y is hydrogen and is in $\beta$-position to the $SO_3H$-group.

15. A process as claimed in claim 1, wherein the compound IV is applied in an amount of from 50 to 150 mole-%, referred to the halide of the bisacid III.

16. A process as claimed in claim 1, wherein the reaction is carried out at a temperature in the range of from 20 to 200°C.

17. A process as claimed in claim 1, wherein the reaction is carried out at a temperature in the range of from 60 to 180°C.

18. A process as claimed in claim 1, wherein the reaction is carried out at a pressure in the range of from ambient pressure to the autogenous pressure of the reaction mixture under the reaction conditions applied.

19. A process as claimed in claim 1, wherein the reaction is carried out at a pressure in the range of from ambient pressure to 15 bar.

20. A process as claimed in claim 1, which is carried out under the exclusion of oxygen.

21. A process for the preparation of halogen-containing aromatic compounds of the formula

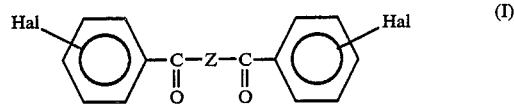

wherein Hal represents fluorine, chlorine or bromine and Z represents an aromatic group, which comprises reacting a halobenzene of the formula $C_6H_5Hal$ (II) under anhydrous conditions with a halide of a bisacid having the formula Hal-CO-Z-CO-Hal (III) in a molar ratio of at least 2:1 in the presence of from 15 to 500 mole-%, referred to the halide of the bisacid III, of a haloalkane sulfonic acid of the formula $Y(C_nF_{2n})SO_3H$ (V), wherein Y is hydrogen and is in $\beta$-position to the $SO_3H$-group, in formulae II and III Hal and Z having the aforementioned meaning and n being an interger of from 1 to 10.

* * * * *